United States Patent [19]

Schnatterer et al.

[11] Patent Number: 5,808,141
[45] Date of Patent: Sep. 15, 1998

[54] PROCESS FOR PREPARING 4,4'-DINITROSTILBENE-2,2'-DISULPHONIC ACID

[75] Inventors: Albert Schnatterer; Helmut Fiege, both of Leverkusen, Germany

[73] Assignee: Bayer Aktiengesellschaft, Leverkusen, Germany

[21] Appl. No.: 897,403

[22] Filed: Jul. 21, 1997

Related U.S. Application Data

[63] Continuation of Ser. No. 585,550, Jan. 11, 1996, abandoned, which is a continuation of Ser. No. 299,771, Sep. 1, 1994, abandoned.

[30] Foreign Application Priority Data

Sep. 8, 1993 [DE] Germany ............... P 43 30 377.3

[51] Int. Cl.$^6$ ............... C07F 11/00; C07G 17/00
[52] U.S. Cl. ............................................. 562/60
[58] Field of Search ................................. 562/60

[56] References Cited

U.S. PATENT DOCUMENTS

| | | |
|---|---|---|
| 4,719,051 | 1/1988 | Guglielmetti . |
| 4,952,725 | 8/1990 | Lund et al. . |
| 5,041,632 | 8/1991 | Guglielmetti . |

FOREIGN PATENT DOCUMENTS

| | | |
|---|---|---|
| 1381730 | 1/1975 | United Kingdom . |
| 2136430 | 9/1984 | United Kingdom . |

*Primary Examiner*—Deborah C. Lambkin
*Assistant Examiner*—Jane C. Osweeki
*Attorney, Agent, or Firm*—Sprung Kramer Schaefer & Briscoe

[57] ABSTRACT

The new process for preparing 4,4'-dinitrostilbene-2,2'-disulphonic acid and salts thereof by oxidation of 4-nitrotoluene-2-sulphonic acid with an oxidant in the presence of strong bases is characterized in that the oxidation is carried out in a mixture of water and an organic solvent selected from the group consisting of alcohols, ethers and mixtures thereof.

7 Claims, No Drawings

PROCESS FOR PREPARING 4,4'-DINITROSTILBENE-2,2'-DISULPHONIC ACID

This application is a continuation of application Ser. No. 08/585,550, filed on Jan. 11, 1996, which is a continuation of application Ser. No. 08/299,771, filed Sep. 1, 1994, both abandoned.

The present invention relates to a new process for preparing 4,4'-dinitrostilbene-2,2'-disulphonic acid and salts thereof.

4,4'-Dinitrostilbene-2,2'-disulphonic acid is an important intermediate for producing optical brighteners. The compound is required in large amounts every year for this application.

Processes for the industrial preparation of 4,4'-dinitrostilbene-2,2'-disulphonic acid (DNS) have been known for a long time. Already at the end of the last century, methods were developed for the oxidative condensation of 2 mol of 4-nitrotoluene-2-sulphonic acid (p-NTSA) in aqueous alkali. Here oxygen (air) was used as oxidant in the presence of a catalyst and hypochlorite or chlorine (cf., for example, Ber. dt. Chem. Ges. 30, 2097–3101 (1897); 31 1079 (1898); DRP 113 514). However, even using modern technology, only unsatisfactory yields of from 60 to 75% of dinitrostilbenedisulphonic acid and salts thereof were able to be achieved using these processes (cf., for example, DE-A 2 258 530).

Newer variants of this process of oxidative condensation of 4-nitrotoluene-2-sulphonic acid give preference to oxygen rather than hypochlorite as oxidant. This development accordingly follows the trend towards cost reduction, since oxygen in the form of air is the cheapest oxidant.

Since in the oxidation with oxygen a solid (salts of 4-nitrotoluene-2-sulphonic acid) is reacted with a gas ($O_2$, air) in the presence of alkali and optionally in the presence of a catalyst, an effective solvent is decisive in the process.

Water is a particularly attractive solvent. On the one hand, the reactants are strongly polar components, on the other hand, they are available particularly cheaply in the form of aqueous solutions or solids moist with water. For example, 4-nitrotoluene-2-sulphonic acid is obtained as an aqueous solution or as a solid moist with water when prepared by sulphonation of 4-nitrotoluene (cf., for example, EP-A 0 083 555). In this case, the 4-nitrotoluene-2-sulphonic acid can be directly introduced into the DNS preparation process without change of solvent and without a further process operation. The handling of alkali and any metal salt catalysts to be used is also carried out particularly economically in the form of aqueous solutions. However, a disadvantage of the process of oxidation in water is the poor solubility of the 4-nitrotoluene-2-sulphonic acid in aqueous sodium or potassium hydroxide solution. Furthermore, to achieve a high selectivity, the process often has to be carried out at low concentrations and low reaction rates, which in the end results in an unsatisfactory space-time yield.

The oxidation with air in aqueous sodium hydroxide solution is described, for example, in a particular process variant in DD 240 200. In a 2-stage process in the presence of catalytic amounts of a manganese salt, oxidation is carried out in the 1st stage at high p-NTS and alkali concentrations with partial precipitation of 4,4'-dinitrobibenzyl-2,2'-disulphonate and in the 2nd stage at low alkali concentration and high dilution. The yields of DNS are given as from 82 to 85% of theory, with the example giving the highest yield in the 2nd reaction stage being carried out at a very low concentration corresponding to 57 g of p-nitrotoluenesulphonic acid per 1000 $cm^3$ of reaction volume. Furthermore, a reaction time of from 8 to 9 hours for the whole process is indicated by the examples.

According to DE-A 3 409 171 the concentration of dinitrostilbenedisulphonic acid in the reaction mixture can be increased to above 30% by weight and the reaction time can be simultaneously shortened if the oxidation by air is carried out in the presence of $Li^+$ ions which are added in a superstoichiometric amount in the form of lithium hydroxide. In the examples shown, the yields are, depending on procedure, up to 86.5% of theory of dinitrostilbenedisulphonic acid. A disadvantage of this process is the additional step for removing the lithium as a lithium carbonate subsequent to the oxidation, the recovery of the lithium carbonate being only 75–80%. To be able to again recycle the lithium to the process, the lithium carbonate has additionally to be converted into lithium hydroxide. The action of the lithium depends in the end on the improved solubility of the lithium salt of p-nitrotoluenesulphonic acid in aqueous alkali.

DE-A 35 195 52 describes a process for preparing dinitrostilbenedisulphonic acid in aqueous suspension, with $K^+$, $Ca^{2+}$ or $Mg^{2+}$ ions being added during the reaction in the amount in which the dinitrostilbenedisulphonic acid is formed. This measure causes precipitation of the dinitrostilbenedisulphonic acid as a sparingly soluble salt. Although the yield of dinitrostilbenedisulphonic acid is high—in one example, which uses a continuous procedure, it is given as 94% of theory—it is again necessary to carry out the reaction at a high dilution of 5–10% of dinitrostilbenedisulphonic acid, which again results in a poor space-time yield in the end. Furthermore, according to the examples, a part of the alkali has to be used in the form of potassium hydroxide which is significantly more expensive than sodium hydroxide.

Apart from water, solvents described are also ammonia and dipolar aprotic solvents.

According to EP-A 0 305 648, the use of liquid, anhydrous ammonia, alkyl derivatives of ammonia and mixtures of these with water as solvent enables the achievement of very high yields of dinitrostilbenedisulphonic acid, which are given in the examples, depending on procedure, as up to 97%. A disadvantage of this process is the use of a solvent which is gaseous at room temperature and under the reaction conditions and for liquefaction has to be handled under pressure. This introduces increased process complications, for example the need to use pressure apparatus. A further disadvantage of the process results from the heat of the reaction being obtained at a very low temperature level because of the low reaction temperatures of from 5–15° C. The heat of reaction, which is characteristically high for oxidation reactions, here has to be absorbed by an energy intensive process, for example by brine cooling.

Similar very high yields of dinitrostilbenedisulphonic acid of up to 98% can be achieved according to EP-A 0 332 137 by carrying out the process in DMSO as solvent or, according to EP-A 0 026 154, by carrying out the process in dipolar aprotic solvents of the acid amide type, in particular DMF as solvent. In both cases, lower alcohols are added to the solvent as co-solvent, with water having to be excluded as far as possible in the DMF process while small amounts of water can be tolerated in the DMSO process; nevertheless, the added amount of water in the examples having the highest yields is less than 0.5% by weight based on the total material used. Working under anhydrous conditions makes high quality demands of the solvents and of the starting materials, for example the nitrotoluenesulphonic acid, the alkali and the air for oxidation. Thus, for example, the solvents have to be made substantially anhydrous prior to use. A decisive disadvantage of the anhydrous process is the use of nitrotoluenesulphonic acid. Nitrotoluenesulphonic acid, which is obtained as an aqueous solution or as a solid moist with water when prepared by the usual processes of sulphonation of nitrotoluene (cf., for example, EP-A 0 083 555), cannot be directly processed further in a form moist with water. Rather, it has to be converted, in a process prior to the oxidation, by means of alkali into the desired salt and subsequently dried. According to EP-A 0 332 137, for example, this process is carried out by neutralization with aqueous sodium hydroxide solution. The sodium salt of nitrotoluenesulphonic acid precipitates as a solid, is separated off from the aqueous mother liquor, taken up in DMSO and dried by distillation. Owing to these expensive additional measures there is no significant economic advantage over the procedure in water, despite the high yields.

There was therefore a need for a process which combines the advantages of the non-aqueous solvents, viz. high space-time yields and high chemical yields, with the advantages of the water process, viz. no solvent change after production of nitrotoluenesulphonic acid, no necessity to use anhydrous starting materials, without it having to be carried out using a solvent, such as ammonia, which is gaseous under the reaction conditions.

The present invention provides a process for preparing 4,4'-dinitrostilbene-2,2'-disulphonic acid and salts thereof of the formula

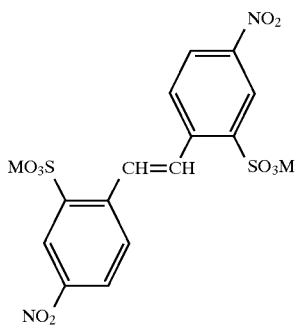

in which

M represents hydrogen or an alkali metal ion, by treating 4-nitrotoluene-2-sulphonic acid with an oxidant in the presence of strong bases, characterized in that the oxidation is carried out in a mixture of water and an organic solvent selected from the group consisting of alcohols, ethers, esters, acetals and mixtures thereof.

The alkali metal ion in the definition of M is preferably lithium, sodium or potassium.

Examples of organic solvents which can be used according to the invention are:
a) from the alcohol class of compounds, the aliphatic alcohols and diols, in particular the monohydric or dihydric, straight-chain or branched, aliphatic alcohols having preferably from 1 to 4 carbon atoms and 1 or 2 OH groups,
b) from the ether class of compounds, the dialkyl ethers each having preferably from 1 to 4 carbon atoms in the straight-chain or branched alkyl part, which are optionally substituted by one or more OH or NE2 groups, such as, for example, methyl tert-butyl ether, 2-methoxyethanol or 2-methoxyethylamine;
also cyclic ethers having from 3 to 5 carbon atoms which can be saturated or olefinically unsaturated, such as, for example, dioxane or furan;

also polyethers, preferably those which correspond to the formula

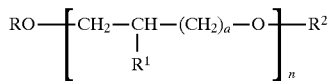

in which

R, $R^1$ and $R^2$, independently of one another, represent straight-chain or branched $C_1$–$C_4$-alkyl, a represents a number from 0 to 2, and
n represents a number from 1 to 8, such as, for example, the dialkyl ethers of ethylene glycol, diethylene glycol, triethylene glycol or octaethylene glycol
c) from the ester compound class, the alkyl esters of lower carboxylic acids, preferably those derived from monohydric or polyhydric, straight-chain or branched, alcohols having from 1 to 4 carbon atoms and 1 to 2 OH groups and straight-chain or branched aliphatic carboxylic acids having 1 to 2 carbon atoms, such as, for example, methyl formate, ethyl formate, methyl acetate, ethyl acetate, trimethyl orthoacetate, dimethyl carbonate or ethylene glycol carbonate
d) from the acetal compound class, preferably those of straight-chain or branched aliphatic alcohols having 1 to 2 carbon atoms and straight-chain or branched aliphatic aldehydes having from 1 to 4 carbon atoms, such as, for example, formaldehyde dimethyl acetal.

Organic solvents preferably used are the $C_1$–$C_4$-alcohols and $C_1$-$C_4$-diols specified under a) and the compounds of the polyether, ether alcohol and ether amine type specified under b). Examples which may be mentioned here are, for the alcohols a), methanol, ethanol, 1-propanol, 2-propanol, 1-butanol, 2-butanol, tert-butanol, for the diols, 1,2-ethanediol, 1,2-propanediol, 1,3-propanediol, 1,2-butanediol, 1,4-butanediol. Examples which may be mentioned of the compounds specified under b) are, for the polyether group, the methyl and ethyl ethers of 1,2-ethanediol, 1,2-propanediol, 1,3-propanediol, 1,2-butanediol, 1,4-butanediol, diethylene glycol, triethylene glycol, polyethylene glycol, polypropylene glycol; for the ether alcohol group, 2-methoxyethanol, 2-ethoxyethanol, diethylene glycol, diethylene glycol monobutyl ether, triethylene glycol, tetraethylene glycol, mixture of octaethylene glycol homologs, propylene glycol 1-methyl ether, propylene glycol 1-ethyl ether, dipropylene glycol; for the ether amine group, 2-methoxyethylamine, 3-methoxypropylamine, 3-ethoxypropylamine, 2-ethoxyethylamine.

The organic solvents a) to d) can be used individually or as a solvent mixture of any composition. Preference is given to the use of mixtures of one or more solvents specified under b) to d) with at least one aliphatic alcohol and/or diol specified under a).

The organic solvent is particularly preferably a mixture of one or more representatives of the group specified under b) of polyethers, ether alcohols and ether amines and one or more representatives of the group of the $C_1$–$C_4$-alcohols and/or $C_1$–$C_4$-diols specified under a). In the organic solvent proportion, the ratio of amounts of the polyether, ether alcohol and ether amine on the one hand to the alcohol and/or diol on the other hand is not subject to any strict limits and is normally such that a sufficient but not necessarily complete solubility of the aqueous and organic solvent proportion is ensured in the process of the invention. The proportion of alcohol and/or diol in the organic solvent can vary between 5 and 90%, preferably between 10 and 80%.

The organic solvents particularly preferably used are ethylene glycol dimethyl ether and/or diethylene glycol dimethyl ether and/or triethylene glycol dimethyl ether in a mixture with methanol and/or 1,2-ethanediol.

The proportion of water in the solvent mixture of water and organic solvent to be used according to the invention can vary over a wide range and is generally between 5 and 95% by weight, preferably between 15 and 90% by weight, particularly preferably between 20 and 80% by weight, in each case based on the sum of the proportions of aqueous and organic solvent.

The 4-nitrotoluene-2-sulphonic acid is preferably introduced into the reaction mixture as an aqueous solution or as a solution in a mixture of water and the organic solvents to be used according to the invention. Furthermore, preference is given to the introduction of the 4-nitrotoluene-2-sulphonic acid as a solid moist with water. Of course, the 4-nitrotoluene-2-sulphonic acid can also be used in the form of metal salts which are formed by neutralization with the strong bases described below, although this variant can comprise an additional process step.

Surprisingly, use of the solvent mixtures of the invention enables results to be achieved in the condensation of 4-nitrotoluene-2-sulphonic acid which are significantly superior to the prior art using water as solvent without the disadvantage of ammonia or the anhydrous process having to be accepted. The reaction rate is, for example, significantly increased in comparison with the process in water; this results not only in a higher space-time yield, but the reaction temperature can be lowered to a level which has not hitherto been described for the process in water. The lower reaction temperature in turn makes possible a more selective reaction with yields above 90% of dinitrostilbenesulphonic acid. A further advantage of the process of the invention is the high dinitrostilbenesulphonic acid concentration in the reaction mixture. The examples given below show that reaction mixtures containing 18% by weight of dinitrostilbenesulphonic acid still give excellent results. The unexpectedly good results are all the more surprising since the previous processes are carried out in organic solvents (cf. EP 0 332 137 and EP 0 026 154), preferably under anhydrous conditions or in the presence of only catalytic amounts of water.

Suitable strong bases are compounds of the alkali and alkaline earth metals, for example metal hydroxides, metal alkoxides and metal amides, and, insofar as the compounds are alkoxides and amides, of aluminium. Important alkali and alkaline earth metals which may be mentioned are, for example, sodium, potassium, lithium, calcium, magnesium. Alkoxides which may be mentioned are, for example, the methoxide, ethoxide, isopropoxide and the propylene glycolate. Among the specified bases, preference is given to the hydroxides; particular preference is given to sodium hydroxide and potassium hydroxide and sodium methoxide. The bases specified can be used individually or in any mixture of them.

The amount of base to be used can vary within wide limits. The amount of base depends, inter alia, on whether the p-nitrotoluenesulphonic acid is used in the acid form or as a salt. Since, when the p-nitrotoluenesulphonic acid is used in the acid form, 1 equivalent of base is consumed in the neutralization of the sulphonic acid group, the base is required in at least equivalent amounts. The base is prefer-ably used in amounts of from 1.5 to 8, preferably from 2 to 5, base equivalents.

Carrying out the process of the invention with addition of a catalyst can be advantageous, but is not absolutely necessary. Catalysts which are used are, in particular, compounds of the transition metals, for example of Co, Mn, Cr, Fe, Ni, Cu, V, Nb, Ta, Ru. Possible forms in which these metals can be used are their salts with inorganic acids, for example the metal fluorides, chlorides, sulphates, nitrates, carbonates, phosphates; the metal oxides and metal hydroxides; the metal salts of organic acids, for example the metal acetates, oxalates, phenoxides, benzoates, salicylates; complexes of these metals with, for example, acetylacetone, N,N'-disalicylidene-ethylenediamine, ethylenediamine, diethylenetriamine, triethylenetetramine, tetraphenylporphine and phthalocyanine.

Of particular importance among the metal catalysts are the compounds of manganese and vanadium.

The oxidant used in the process of the invention can be pure oxygen or oxygen in diluted form, for example in the form of oxygen-containing gases. The most economical form of the oxidant to be used according to the invention is atmospheric air. The pressure of the oxygen or the oxygen-containing gas is not subject to any particular limitation and can be between 0.5 and 20 bar, preferably from 0.8 to 10 bar, particularly preferably near atmospheric pressure. When using oxygen-containing gases, the oxygen content is likewise subject to no limitation. The content and amount of oxygen depends first and foremost on the reaction rate. It is advantageous to finely distribute the oxygen or the air in the reaction mixture, for example using nozzles or frits.

However, the oxygen or the air can also be drawn into the reaction mixture by vigorous stirring using suitable stirrers. The gassing intensity, i.e. the amount of gas made available per unit time, can likewise be greatly varied and depends, for example, on the reactivity of the p-nitrotoluene-2-sulphonic acid in the respective reaction medium used comprising the solvent mixture of the invention, the base and optionally the catalyst. The most favourable gassing conditions for the individual case, for example in respect of the $O_2$ content of the oxidation gas and the gas pressure, can be determined by simple preliminary experiments.

The reaction temperature for the process of the invention can vary between 0 and 100° C. However, the process is preferably carried out at a temperature between 20 and 80° C.

The reaction mixture obtained in the process of the invention can be directly fed into those processes which require dinitrostilbenedisulphonic acid as starting material, for example into the process of the reduction to give 4,4'-diaminostilbene-2,2'-disulphonic acid, which is an important starting material for the production of optical brighteners. Dinitrostilbenedisulphonic acid or salts thereof can, however, also be subjected to intermediate isolation for this purpose. The isolation is carried out according to known process operations and depends, in the individual case, on the organic solvent used. If the salts of dinitrostilbenedisulphonic acid are, for example, sparingly soluble in the reaction mixture, these can be directly separated off as a solid. The remaining mother liquor can optionally be treated with 2-nitrotoluenesulphonic acid and base and recycled to the oxidation step of the process of the invention.

It is likewise possible to remove the organic solvent proportion from the reaction mixture to form an aqueous solution or suspension of the salts of dinitrostilbenedisulphonic acid, optionally by neutralization of excess base with acid and optionally after adding an additional amount of water. Such aqueous solutions or suspensions can be directly further processed in the abovementioned subsequent processes. However, they can also be used for crystallization of the salts of dinitrostilbenedisulphonic acid. The separation of aqueous and organic proportions of solvent is carried out, for example, by distillation or phase separation or by a combination of these process operations. In particular cases it can be advantageous to improve the phase separation by addition of further, preferably nonpolar, solvents.

EXAMPLE 1

A 2 l glass reactor was charged with a mixture of 400 ml of water, 210 g of methanol, 200 g of ethylene glycol dimethyl ether, 0.5 g of manganese(II) sulphate and 90 g of sodium hydroxide at 40° C. While intensively gassing the solution with 40 l of air/h under atmospheric pressure, ¼of a total of 510 g of a 30.5% strength solution of 4-nitrotoluene-2-sulphonic acid in a solvent mixture comprising 72% by weight of water and 28% by weight of ethylene glycol dimethyl ether was metered in over a period of 10 minutes. Subsequently, the temperature was increased over a period of 15 minutes to 50° C. and the remainder of the 4-nitrotoluene-2-sulphonic acid solution was metered in over a period of 1 hour simultaneously with 110 g of a 27.3% strength sodium hydroxide solution. After the metered addition was complete, the mixture was allowed to react further for a total of 5.5 hours at 50° C. with the airstream passed in for gassing being reduced to 20 l/h 30 minutes after the end of the metered addition and to 10 l/h after a further 2 hours. When the reaction was complete, the excess base was neutralized with 80% strength sulphuric acid. The yield of disodium 4,4'-dinitrostilbene-2,2'-disulphonate was, according to HPLC analysis, 90.4% of theory.

EXAMPLE 2

This was carried out as described in Example 1, but with the ethylene glycol dimethyl ether being replaced by diethylene glycol dimethyl ether. The reaction time after the metered addition of the 4-nitrotoluene-2-sulphonic acid was complete was 6 hours.

The yield of disodium 4,4'-dinitrostilbene-2,2'-disulphonate was, according to HPLC analysis, 90.1% of theory.

EXAMPLE 3

This was carried out as described in Example 1, but with the ethylene glycol dimethyl ether being replaced by triethylene glycol dimethyl ether. The reaction time after the metered addition of the 4-nitrotoluene-2-sulphonic acid was complete was 6 hours.

The yield of disodium 4,4'-dinitrostilbene-2,2'-disulphonate was, according to HPLC analysis, 88.1% of theory.

EXAMPLE 4

A 2 l glass reactor was charged with a mixture of 140 ml of water, 290 g of methanol, 250 g of ethylene glycol dimethyl ether, 0.3 g of $VOSO_4.5\ H_2O$ and 107 g of sodium hydroxide at 40° C. While intensively gassing the solution with a gas mixture of 60 l of air and 30 l of nitrogen under atmospheric pressure, ¼of a total of 780 g of a 32.9% strength solution of 4-nitrotoluene-2-sulphonic acid in a solvent mixture comprising 33% by weight of water, 44% by weight of ethylene glycol dimethyl ether and 22% by weight of methanol was metered in over a period of about 10 minutes. Subsequently, the temperature was increased over a period of 15 minutes to 50° C. and the remainder of the 4-nitrotoluene-2-sulphonic acid solution was metered in over a period of 1.5 hours simultaneously with 161 g of a 37.9% strength sodium hydroxide solution. After the metered addition was complete, the mixture was allowed to react further for a total of 3.5 hours at 50° C. During the whole reaction, the airstream passed in was further regulated in such a way that the $O_2$ content in the waste gas leaving the reactor oscillated between 5 and 7% by volume. When the reaction was complete, the excess base was neutralized with 80% strength sulphuric acid. The yield of disodium 4,4'-dinitrostilbene-2,2'-disulphonate was, according to HPLC analysis, 93.2% of theory.

EXAMPLE 5

This was carried out as described in Example 2, but without addition of $VOSO_4$. The yield of disodium 4,4'-dinitrostilbene-2,2'-disulphonate was, according to HPLC analysis, 88.1% of theory.

EXAMPLE 6

This example uses a p-nitrotoluene-2-sulphonic acid concentration of 18% by weight based on the total batch.

A 2 l glass reactor was charged with a mixture of 140 ml of water, 290 g of methanol, 250 g of ethylene glycol dimethyl ether, 0.3 g of $VOSO_4.5\ H_2O$ and 107 g of sodium hydroxide at 40° C. While intensively gassing the solution with a gas mixture of 30 l of air and 30 l of nitrogen under atmospheric pressure, ⅙of a total of 890 g of a 38.4% strength solution of 4-nitrotoluene-2-sulphonic acid in a solvent mixture comprising 45% by weight of water, 36% by weight of ethylene glycol dimethyl ether and 18% by weight of methanol was metered in over a period of about 10 minutes. Subsequently, the temperature was increased over a period of 15 minutes to 55° C. and the remainder of the 4-nitrotoluene-2-sulphonic acid solution was metered in over a period of 3 hours simultaneously with 186 g of a 46.2% strength sodium hydroxide solution. After the metered addition was complete, the mixture was allowed to react further for a total of 3 hours at 55° C. During the whole reaction, the oxidation gas stream was further regulated by variation of the proportions of air and nitrogen in such a way that the $O_2$ content in the waste gas leaving the reactor was between about 5 and 7% by volume. When the reaction was complete, the excess base was neutralized with 80% strength sulphuric acid. The yield of disodium 4,4'-dinitrostilbene-2, 2'-disulphonate was, according to HPLC analysis, 92.7% of theory.

EXAMPLE 7

The reaction was carried out as in Example 6 with the difference that 0.3 g of $MnSO_4.H_2O$ were used as a catalyst (instead of $VOSO_4.5H_2O$). The yield of disodium 4.4'-dinitrostilbene-2,2'-disulphonate was, according to HPLC analysis, 93.9 % of theory.

EXAMPLE 8

A 2 l glass reactor was charged with a mixture of 400 ml of water, 250 g of 1,2-ethanediol, 260 g of ethylene glycol dimethyl ether, 0.3 g of $MnSO4$ and 90 g of sodium hydroxide at 40° C. While intensively gassing the solution with 40 l of air/h under atmospheric pressure, ¼of a total of 510 g of a 32.1% strength solution of 4-nitrotoluene-2-sulphonic acid in a solvent mixture comprising 71% by weight of water and 29% by weight of ethylene glycol dimethyl ether was metered in over a period of about 10 minutes. Subsequently, the temperature was increased over a period of 15 minutes to 55° C. and the remainder of the 4-nitrotoluene-2-sulphonic acid solution was metered in over a period of 1 hour simultaneously with 80 g of a 37.5% strength sodium hydroxide solution. After the metered addition was complete, the mixture was stirred for a further 5 hours at 55° C. with reduction of the airstream to 20 l/h. When the reaction was complete, a dark-coloured solution was present. The excess base was neutralized with 80% strength sulphuric acid, a homogeneous solution was produced from the reaction mixture by addition of a sufficient amount of water and from this solution the yield was determined, by HPLC analysis, as 84.9% of theory.

We claim:

1. A process for preparing 4,4'-dinitrostilbene-2,2'-disulphonic acid and salts thereof of the formula

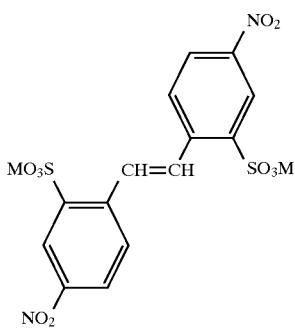

in which

M represents hydrogen, sodium or potassium by treating 4-nitrotoluene-2-sulphonic acid with an oxidant in the presence of sodium hydroxide or potassium hydroxide, wherein the oxidation is carried out in a reaction medium consisting essentially of a mixture of water and an organic solvent selected from the group consisting of,
a) aliphatic alcohols and diols having from 1 to 4 carbon atoms and 1 or 2 OH groups,
b) dialkyl ethers having from 1 to 4 carbon atoms in the straight-chain or branched alkyl part, which are optionally substituted by one or more OH or $NH_2$ groups, cyclic ethers having from 3 to 5 carbon atoms which can be saturated or olefinically unsaturated, and the polyethers corresponding to the formula

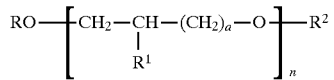

in which

R, $R^1$ and $R^2$, independently of one another, represent straight-chain or branched $C_1$–$C_4$-alkyl, a represents a number from 0 to 2, and n represents a number from 1 to 8.

2. The process according to claim 1, wherein the oxidant used is oxygen or an oxygen-containing gas.

3. The process according to claim 1, wherein the proportion of water in the solvent comprising water and organic solvents is from 5 to 95% by weight preferably from 15 to 90% by weight, based on the mixture.

4. The process according to claim 1, wherein the organic solvents used are selected from the group consisting of ethylene glycol dimethyl ethers, diethylene glycol dimethyl ethers, triethylene glycol dimethyl ethers and mixtures thereof.

5. The process according to claim 1, wherein the organic solvent used is ethylene glycol dimethyl ether, diethylene glycol dimethyl ether, triethylene glycol dimethyl ether or combinations thereof, in a mixture with methanol, 1,2-ethanediol or both.

6. The process according to claim 1, wherein it is carried out in the presence of one or more catalysts selected from the group consisting of transition metal compounds.

7. The process according to claim 1, wherein the catalysts used are compounds of Mn V, or a combination of such compounds in an amount of 0.0001–0.05 molar equivalents, based on the 4-nitrotoluene-2-sulphonic acid.

* * * * *

UNITED STATES PATENT AND TRADEMARK OFFICE
CERTIFICATE OF CORRECTION

PATENT NO.    : 5,808,141
DATED         : September 15, 1998
INVENTOR(S)   : Albert Schnatterer et al.

It is certified that error appears in the above-identified patent and that said Letters Patent is hereby corrected as shown below:

<u>Title page,</u>
Item [22], Filed: delete "Jul. 21, 1997" and substitute -- Jul 22, 1997 --

<u>Column 10,</u>
Line 3, delete "the"
Lines 22-23, after "by weight" delete "preferably from 15 to 90% by weight"
Line 33, delete "triethylene" and substitute -- diethylene --

Signed and Sealed this

Thirteenth Day of August, 2002

*Attest:*

JAMES E. ROGAN
*Director of the United States Patent and Trademark Office*

*Attesting Officer*